United States Patent
Panken et al.

(10) Patent No.: US 6,904,315 B2
(45) Date of Patent: Jun. 7, 2005

(54) ATRIAL AWARE VVI: A METHOD FOR ATRIAL SYNCHRONOUS VENTRICULAR (VDD/R) PACING USING THE SUBCUTANEOUS ELECTRODE ARRAY AND A STANDARD PACING LEAD

(75) Inventors: Eric J. Panken, Edina, MN (US); William J. Combs, Minnetonka, MN (US); Michael B. Shelton, Minneapolis, MN (US)

(73) Assignee: Medtronic, Inc., Minneapolis, MN (US)

( * ) Notice: Subject to any disclaimer, the term of this patent is extended or adjusted under 35 U.S.C. 154(b) by 267 days.

(21) Appl. No.: 09/736,640

(22) Filed: Dec. 14, 2000

(65) Prior Publication Data

US 2002/0123769 A1 Sep. 5, 2002

(51) Int. Cl.[7] .............................. A61N 1/18; A61B 5/04
(52) U.S. Cl. ........................................ 607/9; 600/509
(58) Field of Search ................................ 607/4, 5, 6, 7, 607/9, 11, 25; 600/508, 509, 516, 517, 521

(56) References Cited

U.S. PATENT DOCUMENTS

| | | | |
|---|---|---|---|
| 3,648,707 A | 3/1972 | Greatbatch | |
| 4,059,116 A | 11/1977 | Adams | |
| 4,476,868 A | 10/1984 | Thompson | |
| 4,907,593 A * | 3/1990 | Rapach et al. | 607/19 |
| 5,052,388 A | 10/1991 | Sivula et al. | |
| 5,103,820 A | 4/1992 | Markowitz | |
| 5,172,694 A | 12/1992 | Flammang et al. | |
| 5,331,966 A | 7/1994 | Bennett et al. | 128/696 |
| 5,345,362 A | 9/1994 | Winkler | |
| 5,350,409 A | 9/1994 | Stoop et al. | |
| 5,454,836 A | 10/1995 | van der Veen et al. | |
| 5,489,293 A * | 2/1996 | Pless et al. | 607/5 |
| 5,713,926 A | 2/1998 | Hauser et al. | 607/5 |
| 5,738,105 A * | 4/1998 | Kroll | 600/510 |
| 5,755,739 A | 5/1998 | Sun et al. | |
| 5,778,881 A | 7/1998 | Sun et al. | |
| 5,814,076 A | 9/1998 | Brownlee | 607/9 |
| 6,128,535 A * | 10/2000 | Maarse | 607/28 |
| 6,230,059 B1 * | 5/2001 | Duffin | 607/60 |
| 6,304,778 B1 * | 10/2001 | Gilkerson et al. | 607/5 |
| 6,345,201 B1 * | 2/2002 | Sloman et al. | 607/28 |
| 6,381,493 B1 * | 4/2002 | Stadler et al. | 607/9 |

FOREIGN PATENT DOCUMENTS

| | | | | |
|---|---|---|---|---|
| EP | 0 460 324 A2 | 12/1991 | | A61N/1/05 |
| WO | WO 99/38568 | 8/1999 | | A61N/1/37 |
| WO | WO 00/61225 | * 10/2000 | | |

\* cited by examiner

*Primary Examiner*—Sang Y. Paik
(74) *Attorney, Agent, or Firm*—Girma Wolde-Michael; Paul H. McDowall (57) ABSTRACT

An algorithm is implemented in a circuit for sensing P-waves in a pacemaker to ensure ventricular pacing synchronization with sensed atrial depolarization waves. VDD and VDDR pacing (atrial synchronized, ventricular inhibited pacing) are implemented via a single standard ventricular pacing lead (unipolar or bipolar) and preferably a subcutaneous electrode array (SEA). Specifically, an implanted ventricular lead provides ventricular pacing and ventricular sensing while the SEA enable atrial sensing, thus eliminating the need for an implanted atrial lead or a specialized single pass VDD lead. The algorithm manages the sensed cardiac waves to effect a desired pacing regimen based on the input from the single lead and SEA.

11 Claims, 8 Drawing Sheets

TABLE 1

| PATIENT | INDICATION | CROSSBLANKING + THRESHOLD | | CROSSBLANKING + THRESHOLD + P-WAVE WIDTH | |
|---|---|---|---|---|---|
| | | Sp | Pp | Sp | Pp |
| 302 | AV BLOCK III | 49.1 | 90.0 | 43.5 | 95.0 |
| 303 | AV BLOCK III | 55.3 | 96.6 | 53.4 | 100 |
| 309 | AV BLOCK III | 28.5 | 51.5 | 31.8 | 98.3 |
| 310 | AV BLOCK III | 67.6 | 96.0 | 58.5 | 98.8 |
| 311 | SSS | 89.6 | 98.7 | 86.9 | 100 |
| 315 | SSS | 92.6 | 97.1 | 92.2 | 100 |
| 318 | 2:1 AV BLOCK | 80.7 | 88.3 | 78.7 | 100 |
| 323 | AV BLOCK III | 41.8 | 93.8 | 32.2 | 100 |
| TOTAL | | 68.1 | 90.7 | 64.8 | 99.6 |

SP = SENSITIVITY = # TRUE POSITIVES / # P-WAVES X 100
Pp = POSITIVE SENSITIVITY =# TRUE POSITIVES / (# TRUE POSITIVES + FALSE POSITIVES) X 100

FIG. 8

ATRIAL AWARE VVI: A METHOD FOR ATRIAL SYNCHRONOUS VENTRICULAR (VDD/R) PACING USING THE SUBCUTANEOUS ELECTRODE ARRAY AND A STANDARD PACING LEAD

FIELD OF THE INVENTION

The present invention relates generally to the use of single chamber ventricular-inhibited (VVI) implantable pacemakers to pace the ventricles in synchrony with atrial sensed events (P-waves). Particularly, this invention relates to subcutaneous electrodes used to sense, record, and acquire electrocardiographic data (ECG) and waveform tracings from an implanted VVI pacemaker without the need for or use of surface (skin) electrodes. More particularly, the invention relates to the use of the ECGs and the sensed atrial depolarizations detected by the subcutaneous electrode array (SEA) to implement atrial synchronous ventricular (VDD) pacing in a single chamber VVI pacemaker equipped with a standard VVI pacing lead.

BACKGROUND OF THE INVENTION

The sinus node, where present, intact, and functioning, is the ideal and natural sensor for controlling the heart rate. Often, however, the conduction pathway from the upper chambers (atria) to the lower chambers (ventricles) is blocked, that is, the depolarization signal from the atria cannot reach the ventricles. In such cases, atrial synchronous (VDD) pacing is the only type of pacing required to restore an adequate heart rate. Such pacemakers function as an artificial conduction pathway to reestablish AV synchrony.

VDD pacemakers were first disclosed in U.S. Pat. No. 3,648,707 issued to Wilson Greatbatch, on Mar. 14, 1972, incorporated herein by reference in its entirety. A standard VDD pacemaker requires two electrodes for sensing depolarization signals one within the right atrium and a second in the right ventricle. In general, a standard VDD pacemaker has two sense amplifiers, one for the atrium and one for the ventricle—but only one pacing output circuit for the ventricle. Also included is an A-V interval timer, which starts an AV delay in response to the sensing of an atrial depolarization. On expiration of the A-V interval, a ventricular pacing pulse is triggered, unless inhibited by a sensed R-wave. A sensed or paced R-wave starts a lower rate timer. If this timer expires (that is, without another atrial depolarization being sensed), it triggers a ventricular pacing pulse. The Greatbatch pacemaker also included a ventricular upper rate timer, which prevented or blocked ventricular pacing until the upper rate timeout had expired. In other words, the pacemaker would only pace the ventricle in synchrony with the atrium up to a predetermined upper tracking rate, corresponding to the upper rate interval. If the atrial rate exceeded this rate, the pacing rate would fall to the higher of ½ of the sensed atrial rate or the lower rate.

U.S. Pat. No. 4,059,116 issued to Adams on Jan. 12, 1976, also incorporated herein by reference in its entirety, included an improvement to the pacemaker disclosed in Greatbatch. In the Adams pacemaker, rather than blocking a ventricular stimulus in response to the timeout of the A-V interval during the upper rate interval, generation of a stimulus pulse was delayed until the end of the upper rate interval. That is, the AV interval was extended until the end of the upper rate interval. In addition, a post-ventricular atrial refractory period was included, which specified a period of time following a ventricular pacing pulse or a sensed ventricular contraction, during which an atrial contraction would not be sensed and, thus, could not start an AV interval. The net result of these two additional features was to produce a pacemaker that did not display such an abrupt drop in average ventricular pacing rate in response to an intrinsic atrial rate that exceeded the rate defined by the upper rate interval. The behavior of the Adams pacemaker resembled the natural physiologic condition known as Wenckebach rhythm. In commercially marketed pacemakers employing the Adams invention, the behavior of the pacemaker in the presence of high natural atrial rates is referred to as "Psuedo-Wenckebach" or "Pacemaker-Wenckebach" upper rate behavior.

This standard VDD pacemaker had another issue with regard to the timing. At first, VDD pacemakers had a "fixed" Post Ventricular Atrial Refractory Period (PVARP) following a Premature Ventricular Contraction (PVC). Since PVCs are often followed by a retrograde atrial depolarization, these events, if sensed outside of the fixed PVARP, would start a Pacemaker Mediated Tachycardia (PMT). U.S. Pat. No. 5,103,820 issued to Markowitz in 1992, incorporated herein by reference in its entirety, described a method for programming a programmable period for the PVARP. In addition, this patent also provided a means of automatically extending the PVARP after PVCs that effectively blocks an atrial depolarization from starting an AV interval. As a result, PMTs resulting from retrograde atrial depolarizations after such PVCs virtually ceased to be an issue.

Throughout this period of time, the VDD pacemakers known in the art up to 1992 required two leads, one in the atrium and a second in the ventricle. Implanting two leads extended the time for the implant procedure, as well as the possibility for complications during and post implantation. This was particularly true of the atrial lead, which is more prone to dislodgement. Such dislodgement, when it occurred, reduced the operation of the VDD pacemaker to that of a standard VVI pacemaker. Moreover, the use of two leads increased the cost of the VDD pacing system.

U.S. Pat. No. 5,172,694 issued to Flammang in 1992 and U.S. Pat. No. 5,454,836 issued to Van der Veen in 1995, both incorporated herein by reference in their entirety, describe the use of a single lead for atrial sensing and ventricular pacing. Specifically, it is a single dual chamber lead for providing reliable ventricular sensing and pacing from a lead in the right ventricle and atrial sensing from at least two locations in the atrium to determine P-wave direction and conduction time. While this "single pass" VDD lead represented an advance in the art, it unfortunately was often difficult to use. Although the implantation process resembled that of a single standard ventricular lead, positioning the "floating" electrodes within the atrium to provide adequate sensing was often difficult. Moreover, once properly positioned, there was no guarantee that these electrodes would remain in the optimal position since there was no way to affix the electrodes to the wall or floor of the atrium. This new lead also was more difficult to manufacture and, as a result, did not significantly reduce the cost of the VDD pacing system.

A more recent development involves the addition of rate responsive (VDDR) pacing to the standard VDD pacing. U.S. Pat. No. 5,350,409 issued to Stoop, et al. in 1995 describes one such embodiment. The basis of VDDR pacing is to provide a ventricular rate via an artificial sensor (activity, accelerometer, minute ventilation, QT, etc.) to match the patient's physiologic needs in the absence of a healthy sinus node. The issue to be resolved is to ensure that the sensor-indicated rate does not conflict with the sinus rate.

This Stoop patent discloses how the sensor-indicated rate is adjusted as a function of sensed sinus rate. The natural sinus rate is compared to the sensor-indicated rate at one or more rates, and the sensor response function is adjusted, or adapted as a function of such comparisons, so as to optimize sensing of the atrial rate and maintenance of synchronous operation. Again, however, the issue is whether or not the atrial depolarization wave has been sensed. Undersensing or loss of sensing on the atrial lead could potentially lead to a loss of AV synchrony.

SUMMARY OF THE INVENTION

It has always been the goal in pacing to use the ideal sensor, that is, the sinus node. Physiologic pacemakers (VDD and DDD) i.e., pacemakers that use the sinus, are truly rate responsive and provide AV synchrony thereby avoiding "Pacemaker Syndrome," a combination of debilitating symptoms often associated with single chamber VVI pacing. The present invention comprises an algorithm and circuit for sensing P-waves in a VVI pacemaker so as to ensure ventricular pacing in synchrony with these sensed atrial depolarizations. This invention thereby provides VDD and VDDR pacing (atrial synchronized, ventricular inhibited pacing) via a single standard ventricular pacing lead (unipolar or bipolar) and a Subcutaneous Electrode Array (SEA). The implanted ventricular lead provides for ventricular pacing and ventricular sensing only. Atrial sensing, which is required for VDD/R function occurs via a Subcutaneous Electrode Array described in the following patent applications: Ser. No. 09/697,438, filed Oct. 26, 2000, entitled Surround Shroud Connector and Electrode Housings for a Subcutaneous Electrode Array and Leadless ECGs; Ser. No. 09/703,152, filed Oct. 31, 2000, entitled Subcutaneous Spiral Electrode for Sensing Electrical Signals of the Heart; Ser. No. 09/696,365, filed Oct. 25, 2000, entitled Multilayer Ceramic Electrodes for Sensing Cardiac Depolarization Signals; patent application entitled Thin Film Electrodes for Sensing Cardiac Depolarization Signals, filed Dec. 13, 2000; and Ser. No. 09/721,275, filed Nov. 22, 2000, entitled Subcutaneous Electrode Array Virtual ECG Lead. The present invention eliminates the need for an implanted atrial lead or a specialized "single pass" VDD lead.

In general, the present invention uses a single chamber ventricular-inhibited (VVI) pacemaker that is adapted to furnish atrial synchronous (VDD) pacing by sensing native atrial depolarization waves (P-waves) and pacing the ventricles in synchrony with the sensed P-waves. These P-waves, rather than being detected by a second implanted lead or using the ventricular electrogram to differentiate the atrial signal via an algorithm, are detected by the subcutaneous electrode array (SEA) located on the implanted VVI pacemaker. Briefly, the Subcutaneous Electrode Array (SEA) detects P-waves along with any intrinsic or paced R- and T-waves (QRST). A novel sensing circuit, which constitutes a significant part of the present invention, distinguishes P-waves from intrinsic and/or paced R-waves (QRS) as well as ventricular repolarization (T) waves. In addition, this same sensing circuit is able to differentiate P-waves from other electronic noise (myopotentials). In the absence of sensed P-waves (as when the atrial rate falls below the lower or sensor-indicated pacing rate) and as occurs in every VDD/R pacing system, VVI/R pacing only will ensue.

Accordingly, this invention provides, inter alia, a method of detecting substantially all and every valid and true atrial depolarization wave and synchronizing a ventricular pacing output to this sensed event. In the absence of such a sensed atrial event, the invention provides a ventricular paced output either at the lower (VDD) or sensor-indicated (VDDR) rate. Further, the invention promotes efficiencies in the manufacture and implantation of the pacemaker and lead thereby reducing the cost of the pacemaker system. Furthermore, the invention provides AV synchrony while using a true single chamber pacing system, thereby reducing current drain and increasing the longevity of the device, thus reducing the number of replacements and associated costs of such replacements.

DETAILED DESCRIPTION OF THE DRAWINGS

Figure 1:
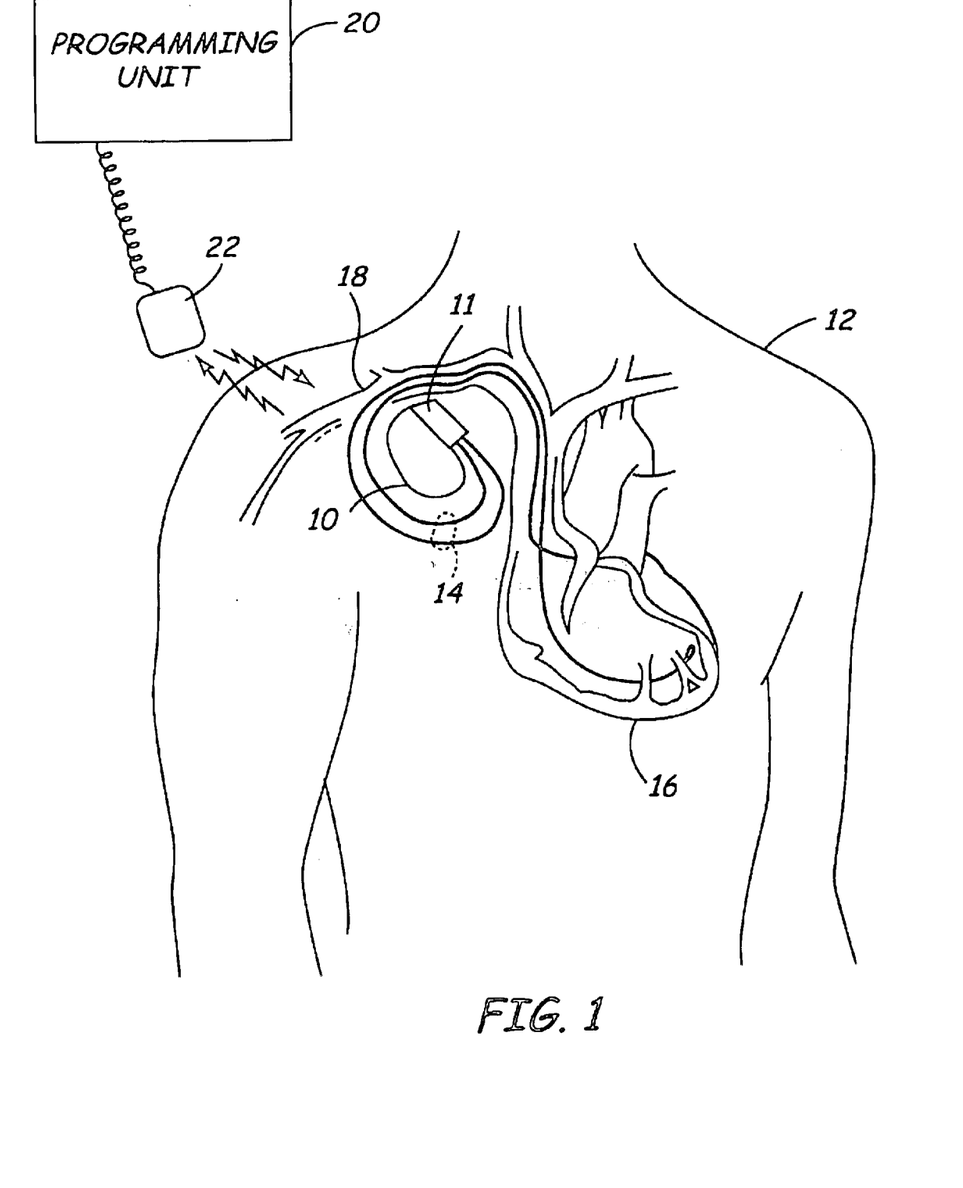
FIG. 1 is an illustration of a body-implantable device system in accordance with the present invention, including a hermetically sealed device implanted in a patient and an external programming unit.

FIG. 1 is an illustration of an implantable medical device system adapted for use in accordance with the present invention. The medical device system includes an implantable, modified VVI pacemaker 10 implanted in a patient 12. One ventricular pacemaker lead 14 is electrically coupled to pacemaker 10 in a conventional manner and extends into the patient's heart 16 via a vein 18. Near the distal end of lead 14 are one or more exposed conductive electrodes for receiving electrical cardiac signals and/or for delivering electrical pacing stimuli to heart 16.

Also depicted in FIG. 1 is an external programming unit 20 for non-invasive communication with implanted device 10 via uplink and downlink communication channels. Associated with programming unit 20 is a programming head 22 for facilitating two-way communication between implanted device 10 and programmer 20.

Figure 2:
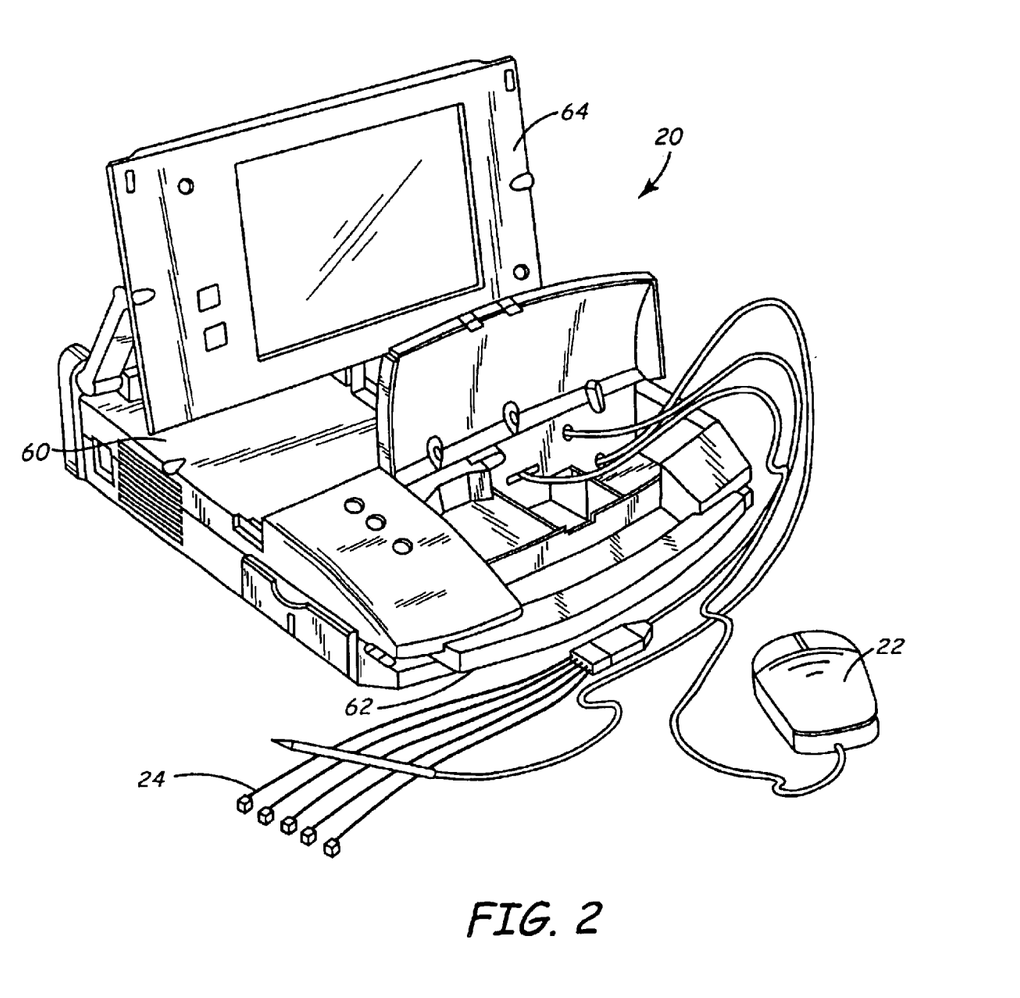
FIG. 2 is a perspective view of the external programming unit of FIG. 1.

FIG. 2 is a perspective view of programming unit 20 in accordance with the presently disclosed invention. Internally, programmer 20 includes a processing unit (not shown in the Figure) that in accordance with the presently disclosed invention is a personal computer type motherboard, e.g., a computer motherboard including a microprocessor such as an Intel Pentium 3 and related circuitry such as digital memory. The details of design and operation of the programmer's computer system will not be set forth in detail in the present disclosure, as it is believed that such details are well-known to those of ordinary skill in the art.

Referring to FIG. 2, programmer 20 comprises an outer housing 60 and a carrying handle 62, so programmer 20 can be carried like a briefcase. An articulating display screen 64 is disposed on the upper surface of housing 60. As would be appreciated by those of ordinary skill in the art, display screen 64 is operatively coupled to the computer circuitry disposed within housing 60 and is adapted to provide a visual display of graphics and/or data under control of the internal computer.

As would be appreciated by those of ordinary skill in the art, it is often desirable to provide a means for determining the status of the patient's conduction system. Normally, programmer 20 is equipped with external ECG leads 24. It is these leads that are rendered redundant by the present invention (as indicated by the large X). The ECG tracings from the SEA are used in their stead.

In accordance with the present invention, programmer 20 is equipped with an internal printer (not shown) so that a hard copy of a patient's ECG or of graphics displayed on the programmer's display screen 64 can be generated. Several types of printers, such as the AR-100 printer available from General Scanning Co., are known and commercially available.

Programmer 20 described herein with reference to FIG. 2 is described in more detail in U.S. Pat. No. 5,345,362 issued to Thomas J. Winkler, entitled "Portable Computer Apparatus With Articulating Display Panel," which patent is hereby incorporated herein by reference in its entirety. The Medtronic Model 9790 programmer is the implantable device-programming unit with which the present invention may be advantageously practiced.

Figure 3:
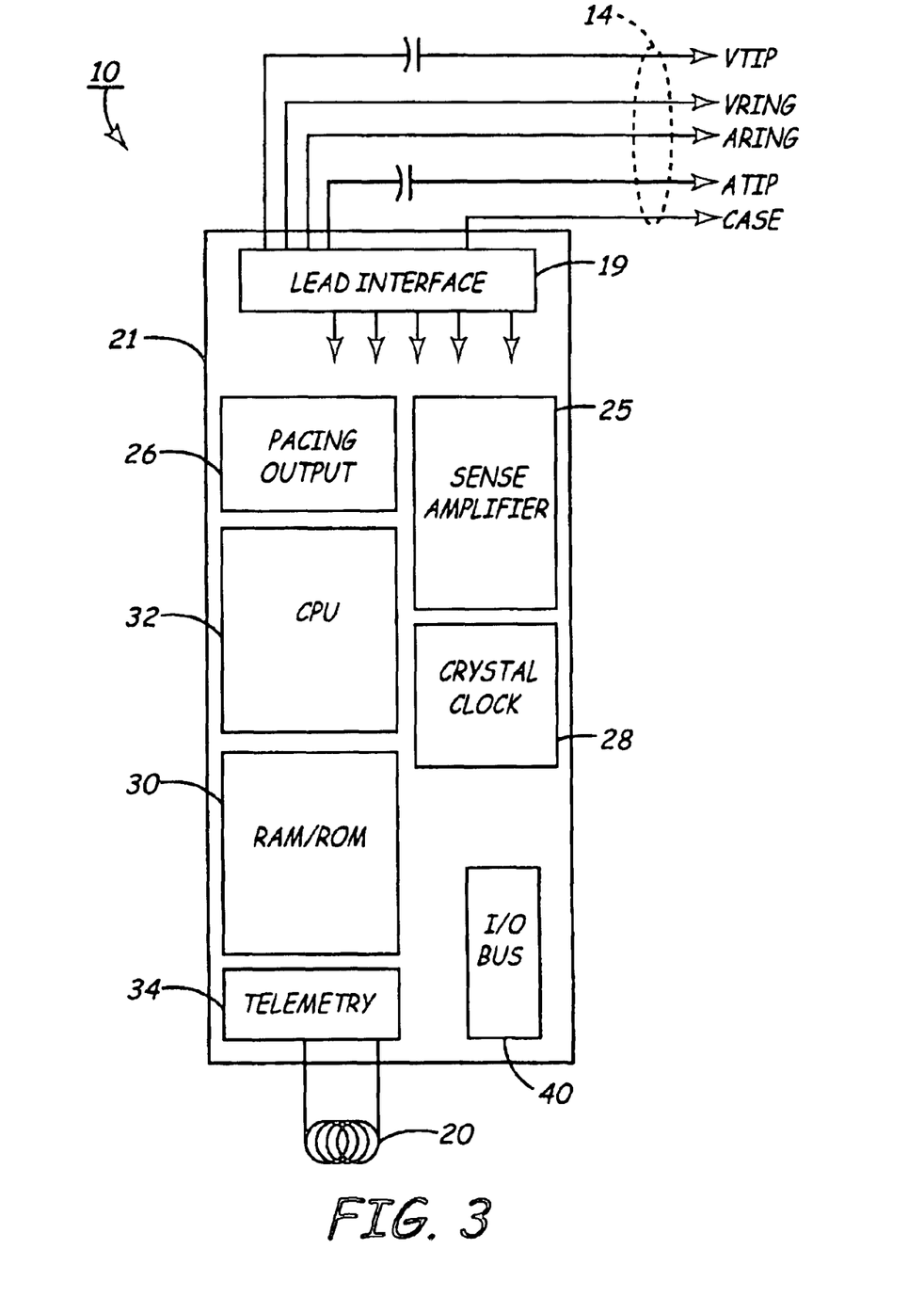
FIG. 3 is a block diagram of the implanted device from FIG. 1.

FIG. 3 is a block diagram of the electronic circuitry that makes up pulse generator 10 in accordance with the presently disclosed invention. As can be seen from FIG. 3, pacemaker 10 comprises a primary stimulation control circuit 21 for controlling the device's pacing and sensing functions. The circuitry associated with stimulation control circuit 21 may be of conventional design, in accordance, for example, with what is disclosed U.S. Pat. No. 5,052,388 issued to Sivula et al., "Method and apparatus for implementing activity sensing in a pulse generator." To the extent that certain components of pulse generator 10 are conventional in their design and operation, such components will not be described herein in detail, as it is believed that design and implementation of such components would be a matter of routine to those of ordinary skill in the art. For example, stimulation control circuit 21 in FIG. 3 includes stimulating pulse output circuitry 26, a crystal clock 28, a random-access memory and read-only memory (RAM/ROM) unit 30, and a central processing unit (CPU) 32, all of which are well-known in the art.

Pacemaker 10 also includes internal communication circuit 34 so that it is capable communicating with external programmer/control unit 20, as described in FIG. 2 in greater detail.

With continued reference to FIG. 3, pulse generator 10 is coupled to one ventricular lead 14 which, when implanted, extends transvenously between the implant site of pulse generator 10 and the patient's heart 16, as previously noted with reference to FIG. 1. Physically, the connections between lead 14 and the various internal components of pulse generator 10 are facilitated by means of a conventional connector block assembly 11, shown in FIG. 1. Electrically, the coupling of the conductors of lead 14 and internal electrical components of pulse generator 10 may be facilitated by means of a lead interface circuit 19 which functions, in a multiplexer-like manner, to selectively and dynamically establish necessary connections between various conductors in leads 14, including ventricular tip and ring electrode conductors VTIP and VRING, and individual electrical components of pulse generator 10, as would be familiar to those of ordinary skill in the art. For the sake of clarity, the specific connections between lead 14 and the various components of pulse generator 10 are not shown in FIG. 3, although it will be clear to those of ordinary skill in the art that, for example, lead 14 will necessarily be coupled, either directly or indirectly, to sense amplifier circuitry 25 and stimulating pulse output circuit 26, in accordance with common practice, such that cardiac electrical signals may be conveyed to sensing circuitry 25, and such that stimulating pulses may be delivered to cardiac tissue, via leads 14. Also not shown in FIG. 3 is the protection circuitry commonly included in implanted devices to protect, for example, the sensing circuitry of the device from high voltage stimulating pulses.

As previously noted, stimulation control circuit 21 includes central processing unit 32 which may be an off-the-shelf programmable microprocessor or micro controller, but in the present invention is a custom integrated circuit. Although specific connections between CPU 32 and other components of stimulation control circuit 21 are not shown in FIG. 3, it will be apparent to those of ordinary skill in the art that CPU 32 functions to control the timed operation of stimulating pulse output circuit 26 and sense amplifier circuit 25 under control of programming stored in RAM/ROM unit 30. It is believed that those of ordinary skill in the art will be familiar with such an operative arrangement.

With continued reference to FIG. 3, crystal oscillator circuit 28, in the presently preferred embodiment a 32,768-Hz crystal controlled oscillator provides main timing clock signals to stimulation control circuit 21. Again, the lines over which such clocking signals are provided to the various timed components of pulse generator 10 (e.g., microprocessor 32) are omitted from FIG. 3 for the sake of clarity.

It is to be understood that the various components of pulse generator 10 depicted in FIG. 3 are powered by means of a battery (not shown) that is contained within the hermetic enclosure of pacemaker 10, in accordance with common practice in the art. For the sake of clarity in the Figures, the battery and the connections between it and the other components of pulse generator 10 are not shown.

Stimulating pulse output circuit 26, which functions to generate cardiac stimuli under control of signals issued by CPU 32, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits that would be suitable for the purposes of practicing the present invention.

Figure 5:
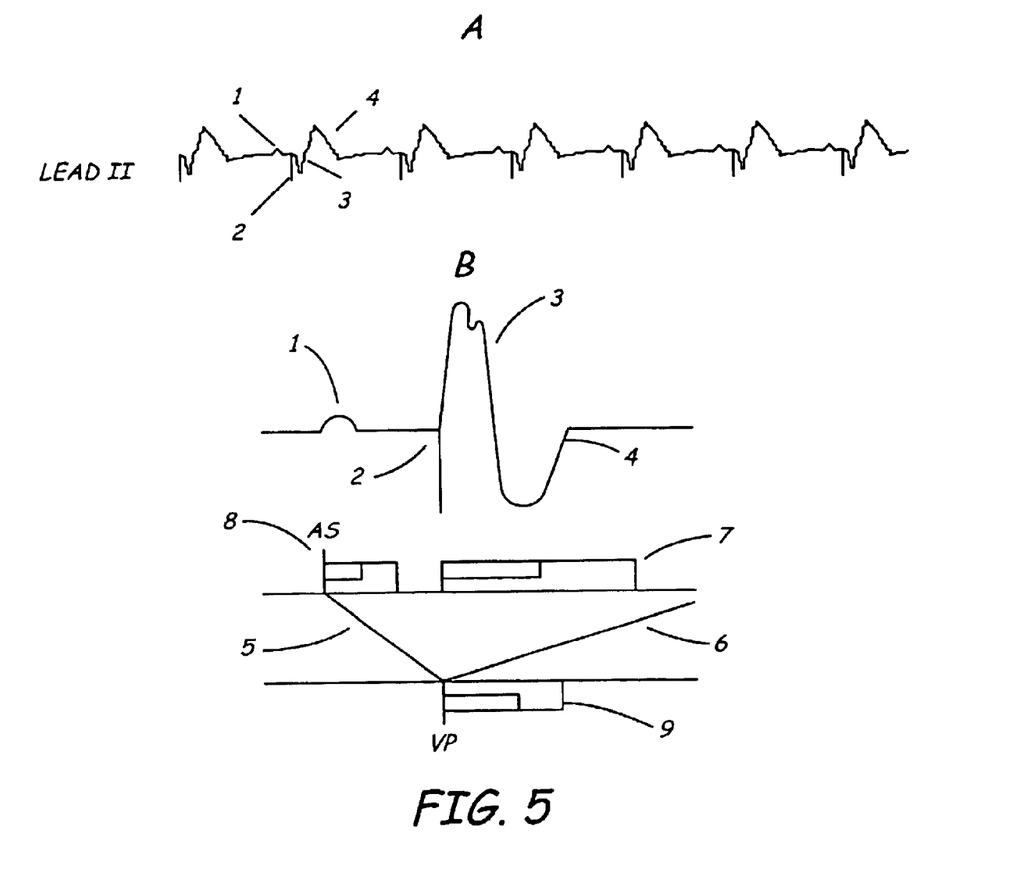
FIG. 5 is an ECG tracing depicting atrial synchronous (VDD) pacing (on Lead II) obtained from the external programming unit of FIG. 2, and a timing diagram thereof.
Figure 6:
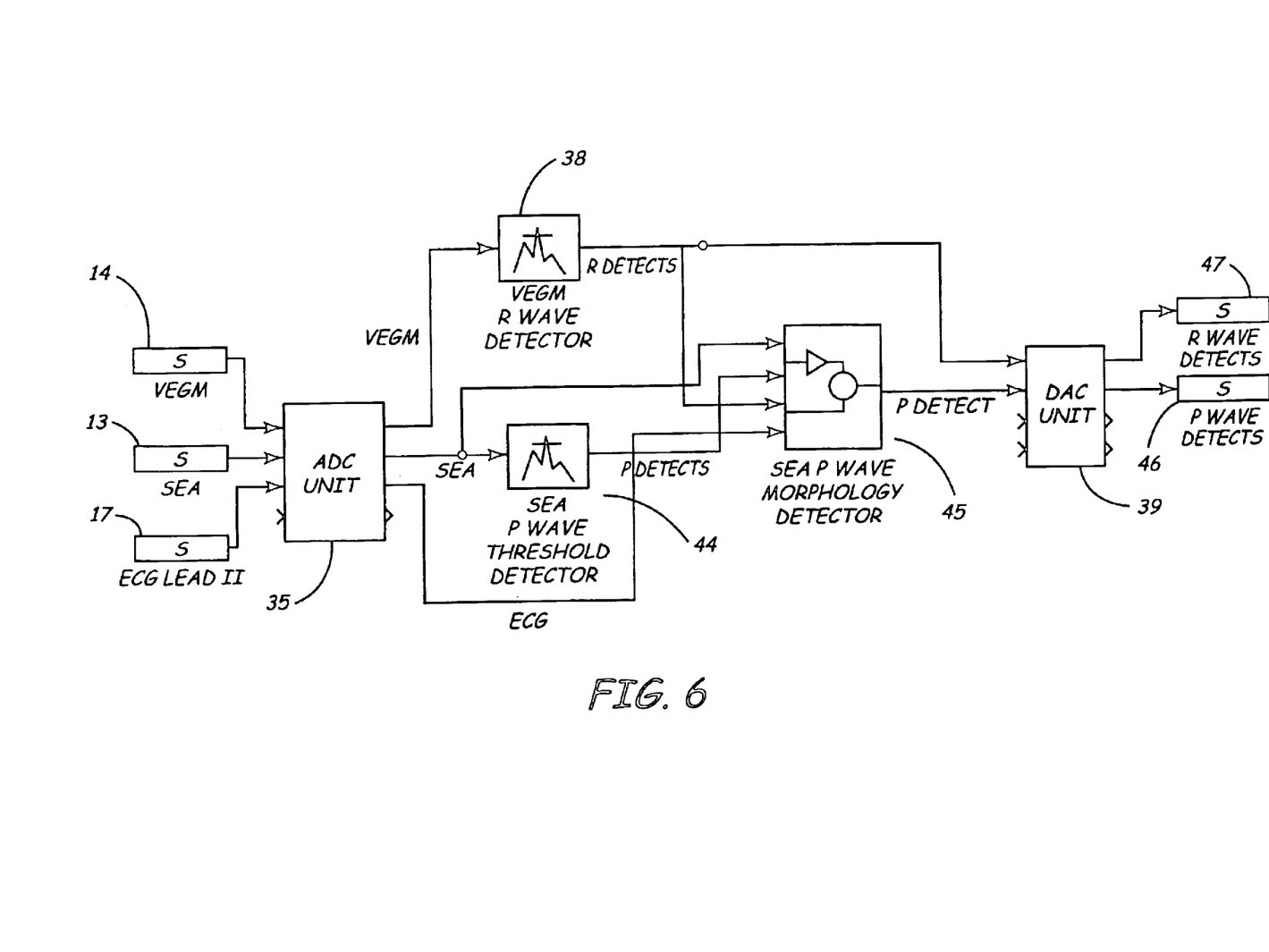
FIG. 6 is a block diagram of the sensing circuit practiced within the present invention.
Figure 7:
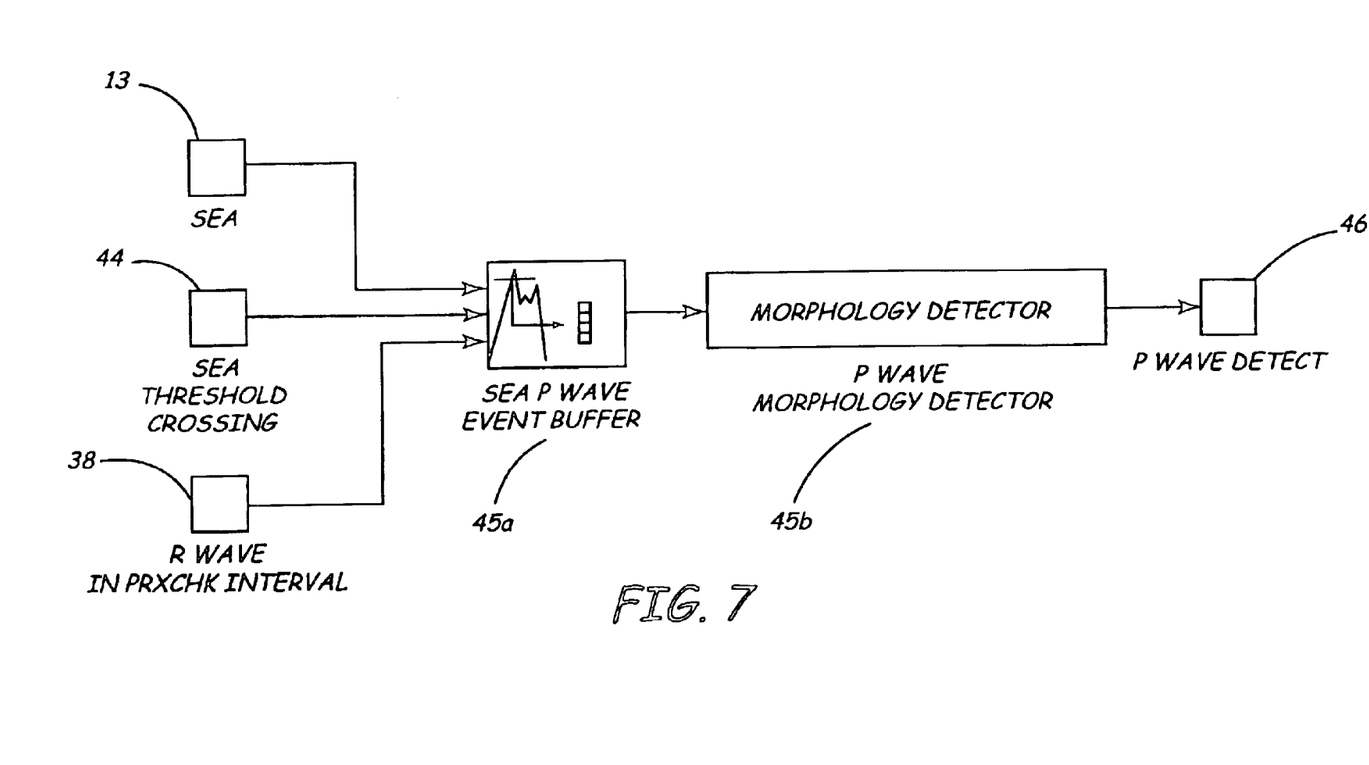
FIG. 7 is a detailed block diagram of the SEA P-wave morphology detector circuit.

Sense amplifier circuit 25, which is of novel design and further discussed in FIGS. 6 and 7, functions to receive electrical cardiac signals from ventricular lead 14 and SEA (not shown) and to process such signals to derive event signals reflecting the occurrence of specific cardiac electrical events, including atrial depolarizations (P-waves) and ventricular depolarizations (R-waves). CPU provides these event-indicating signals to CPU 32 for use in controlling the synchronous stimulating operations of pulse generator 10 in accordance with common practice in the art. In addition, these event-indicating signals may be communicated, via uplink transmission, to external programming unit 20 for visual display to a physician or clinician (as shown in FIG. 5).

Those of ordinary skill in the art will appreciate that pacemaker 10 may include numerous other components and subsystems, for example, activity sensors and associated circuitry. The presence or absence of such additional components in pacemaker 10, however, is not believed to be pertinent to the present invention, which relates primarily to the implementation and operation of sensing circuitry 25 in pacemaker 10, and an associated communication subsystem in external unit 20.

Figure 4:
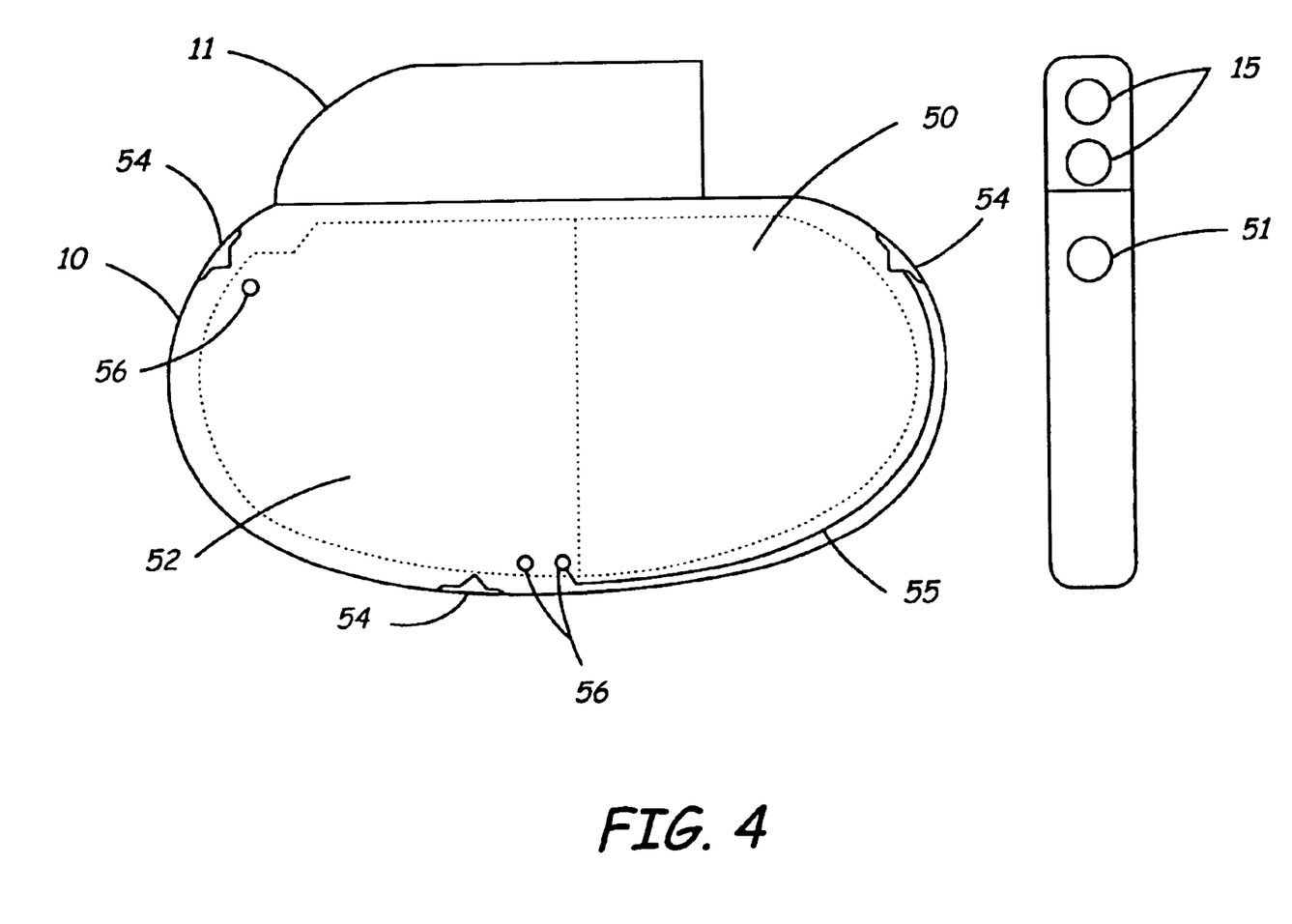
FIG. 4 is a cross sectional view of an implanted pacemaker in which the present invention may be practiced.

FIG. 4 is a cross sectional view of implanted pacemaker 10 in which the present invention may be practiced. The major components of pacemaker 10 consist of a hermetic casing in which are housed electronic circuitry 52 and a hermetic power source 50, in this case, a lithium-iodine battery. Lead connector module 11 provides an enclosure into which proximal ends of atrial and ventricular leads may be inserted into openings 15. Lead connector module is connected to pacemaker casing 10 and has electrical connections (not shown) between lead connectors and hermetic feedthroughs (also not shown).

Continuing with FIG. 4, three or four (not shown) feedthrough/electrode assemblies 51 are welded into place on the flattened periphery of the pacemaker casing. In this embodiment, the complete periphery of the pacemaker may be manufactured to have a slightly flattened perspective with rounded edges to accommodate the placement of feedthrough/electrode assemblies such as those practiced in the present invention. These feedthrough/electrode assemblies 54 are welded to pacemaker casing (to preserve hermeticity) and are connected via wire 55 through feedthroughs 56 to electronic circuitry 52.

FIG. 5a is an ECG tracing depicting atrial synchronous (VDD) pacing (on Lead II) obtained from the external programming unit of FIG. 2. The operation depicted in this figure is typical of what those familiar with the state of the art would expect to see on an ECG tracing taken from Lead vector II. A native atrial depolarization 1, also called a P-wave, occurs at a rate within a normal range (for example, between 50 and 120 beats a minute). P-wave 1 starts AV interval timing 5 (FIG. 5b), which culminates in ventricular pacing pulse 2. Ventricular pacing pulse 2 causes ventricular depolarization (paced R-wave) 3 and repolarization (T-wave) 4. This sequence of events is termed atrial synchronous or VDD pacing.

FIG. 5b depicts underlying timing sequences that are used in VDD pacing to ensure normal and correct operation. AV interval timing 5 is typically programmable and is the period of time between sensed P-wave 1 and ventricular output pulse 2. Period 8, following a sensed P-wave, normally has an atrial blanking period (shaded area) in a standard VDD pacemaker with an atrial lead. Such a blanking period is required because an atrial lead might "double sense" a P-wave. The present invention, although it has no atrial lead, still requires such a blanking period. In normal VDD pacing, ventricular pacing pulse 2 starts VA interval timing 6, as well as post-ventricular atrial refractory period (PVARP) 7 with its associated post-ventricular blanking period (shaded area) and ventricular refractory period 9 and its associated blanking period (shaded area). In the present invention, a P-wave threshold crossing starts a PR cross check interval (see FIGS. 6 and 7). If an R-wave is detected in the PR cross check interval, the P-wave is ignored because an R-wave has been detected—not a P-wave. PVARP interval 9, with its associated blanking period (shaded area), is triggered by such a detected R-wave and is present in the present invention. PVARP interval 9 is also used to blank retrograde P-waves, thereby providing protection against pacemaker-mediated tachycardia (PMT). VA interval timing normally terminates with sensed P-wave 1. If no P-wave is sensed, VA interval 6 is extended by AV interval period 8 and ventricular pacing pulse 2 is emitted. The absence of a sensed P-wave could be due to several causes, e.g., sinus bradycardia, sinus pause, sinus block, etc. Post-ventricular atrial refractory period 7 generally serves two purposes. Its associated blanking period is meant to prevent sensing of ventricular pacing pulse 2, commonly called "far-field R-wave sensing." Such sensing, if allowed to occur, could be interpreted by the pacemaker as another P-wave to which it would synchronize a ventricular output pulse, leading to a form of pacemaker mediated tachycardia (PMT). The period of time after the blanking period is called by various terms, among them, "noise sampling period." Atrial events, sensed within this period will not start AV interval timing 5. Ventricular refractory period 9 also has an associated blanking period (shaded area). The purpose of this blanking period is to prevent self-inhibition, that is, sensing of ventricular pacing pulse 2 and paced r-wave 3. The remaining portion of ventricular refractory period 9 is also a noise sampling period. Any R-wave sensed in this period resets, or restarts, the ventricular refractory period.

This brief description of the underlying timing of VDD pacing will serve as a touchstone for further art. Each of these vital timing sequences, as well as others to be mentioned as appropriate to the art, must be accounted for to ensure VDD pacing in the absence of an atrial lead within the heart.

FIG. 6 is a block diagram of the electronic sensing circuitry used in pulse generator (10) in accordance with the presently disclosed invention. There are three signal inputs to the analog-digital converter (ADC) unit 35. The ventricular electrogram (VEGM) is a primary input and is transmitted via the ventricular lead (14) located in the apex of the right ventricle. This signal input consists of the intrinsic ventricular depolarization waveform which, when received and processed, inhibits the scheduled ventricular output pulse. Subcutaneous electrode array (SEA) 13 is also a primary input and provides ECG data to the ADC on a continuous basis. ECG Lead II 17 is a secondary input and is used for auto setup of the detection parameters. Lead II 17 is preferably an external electrode from programmer 20 that could be used to validate the readings from the SEA.

Continuing with FIG. 6, we will follow the ventricular electrogram signal. This signal is first transmitted to ADC unit 35 that has a sampling rate of 250 Hz with a 16-bit resolution. The present invention, however, does not partition the manner in which signal processing tasks are performed, that is, ADC or DAC. The ventricular EGM signal is transmitted to VEGM High Pass Filter 36 that has a pass band from 3 to 100 Hz. The filtered signal goes through VEGM to VEGM R-wave detector 38 that determines if the amplitude of the sensed R-wave has exceeded the programmed ventricular sensitivity and therefore is "sensed." In addition to sending the ventricular sensed signal to DAC unit 39, the circuit also transmits the ventricular sensed signal to SEA P-wave threshold detector 44 for cross checking. The detected R-wave signal is used to blank the QRST complex from the SEA signal at SEA P-wave threshold detector 44.

Turning our attention to the atrial signal, we note that both SEA 13 and ECG Lead II signals 17 must be preprocessed to ensure appropriate sensing of a valid atrial depolarization signal (P-wave). Both signals are passed through ADC unit 35 for conversion, and from there to SEA bandpass filter 41 which has a pass band from 0.5 to 40 Hz. ECG Lead II signal input may be used to set up the P-wave detector parameters automatically. SEA P-wave threshold detector 44 receives the R-wave threshold detection signal from the VEGM R-wave detector 38. SEA P-wave threshold detector 44 uses this signal to blank the ventricular portion of the signal (QRST complex) from the SEA signal. Thus, the portion of the SEA signal that is not cross-blanked is the P-wave. The atrial signal is compared to stored samples within SEA P-wave morphology detector 45. The decision as to whether the signal is a valid P-wave is based either on the width of the signal or one of various morphology metrics that may be programmed by the clinician. Assuming, however, that the signals are deemed valid, they are sent out to stimulation control unit (21). P-wave detects 46 initiate an AV interval, whereas the R-wave detects 47 serve to inhibit the scheduled ventricular output pulse.

FIG. 7 is a detailed block diagram of SEA P-wave morphology detector circuit 45, comprised of two sub blocks. SEA P-wave event buffer 45a has both a circular and linear data buffer. SEA data is continuously stored in the circular buffer until a P-wave threshold crossing occurs 44. At that time, the circular buffer is frozen and the linear buffer starts to fill. The linear buffer freezes after a set number of samples are stored. When frozen, event buffer 45a contains a potential P-wave. The potential P-wave in event buffer 45a is then analyzed by P-wave morphology detector 45b to determine if a valid P-wave is present.

P-wave morphology detector 45b decision function is based either on the width of the signal in event buffer 45a of one of various morphology metrics. The width is defined as the duration of the minimum window about the P-wave threshold crossing 44 point where the signal at the left endpoint of the window is at or below the baseline value. The baseline is assumed to be zero (0), but can be determined adaptively. If the user selects a morphology metric, the potential P-wave in event buffer 45a is compared to a P-wave template using the selected metric. These metrics are: correlation, absolute difference, or mean square difference and are defined as follows.

| Morphology Metric | Definition (Si = ith signal sample, Ti = ith template sample) |
|---|---|
| Correlation | $Corr(S, T) = \sum_{i=1}^{N} (S_i - \bar{S})(T_i - \bar{T})$ |
| Absolute Difference | $AbsDiff(S, T) = \sum_{i=1}^{N} |S_i - T_i|$ |
| MeanSquare | $Mse(S, T) = \sum_{i=1}^{N} (S_i - T_i)^2$ |

The template samples Ti are determined during the auto-setup procedure. Morphology matching is disabled until N P-waves are detected using cross blanking, amplitude threshold, and P-wave width. The P-wave template is the average of these N beats. Morphology matching is enabled after the template is constructed.

Figure 8:
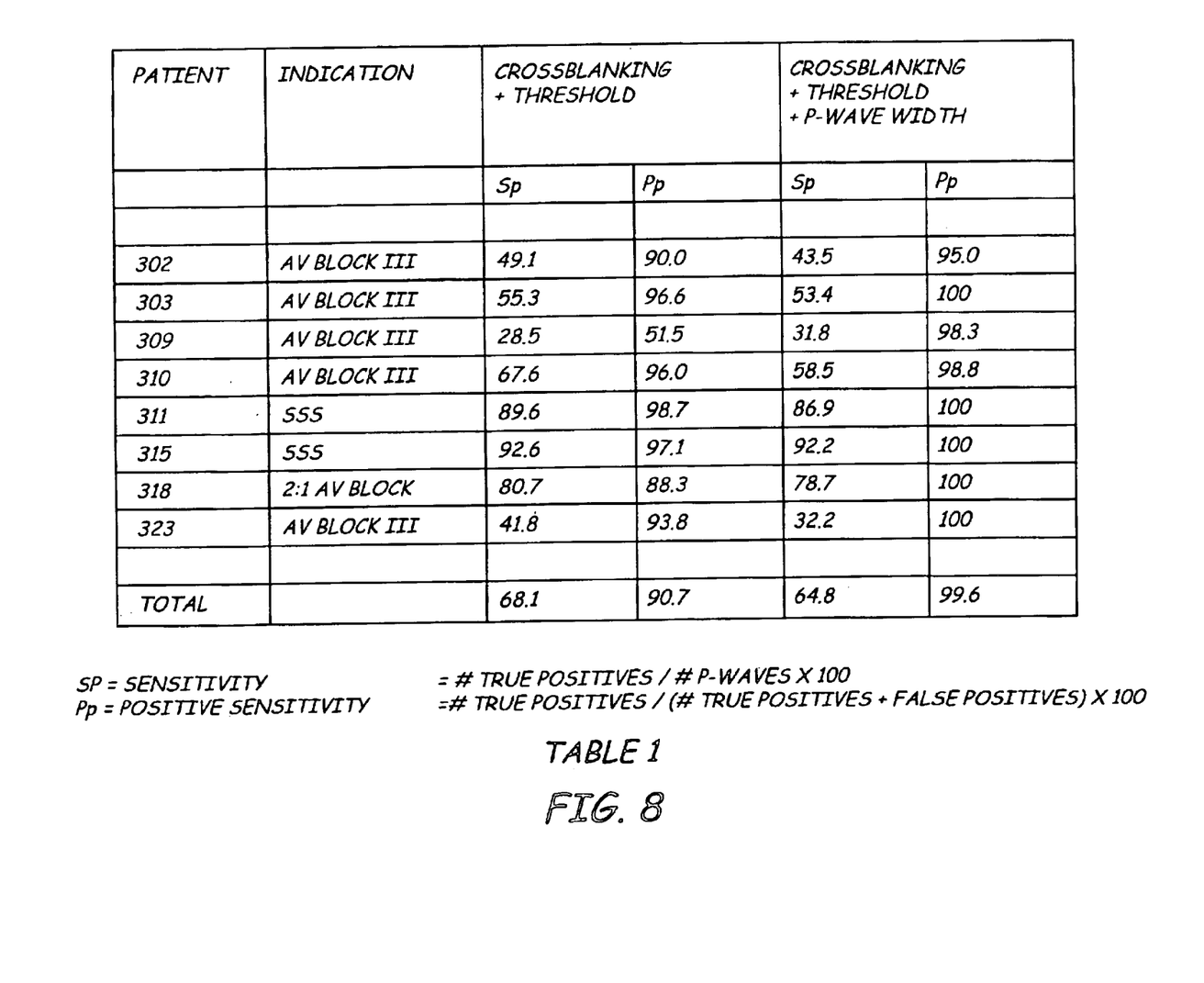
FIG. 8 is a TABLE 1 of a summary of the open loop performance of the P-wave detectors described in FIGS. 6 and 7.

TABLE 1 summarizes the open loop performance of the P-wave detectors described in FIGS. 6 and 7. Open loop performance, as used herein, means that the sensitivity/specificity of the P-wave detector is determined and maintained by post-processing of the data—not by AV synchrony. During testing of the P-wave detector, atrial and ventricular activity are asynchronous. Column three (Cross blanking+ Threshold) displays the performance of the threshold and cross blank method. This method blanks the QRST portion of the SEA signal; P-waves are then detected using a simple threshold-crossing criterion. Column 4 (Cross blanking+ Threshold+P-wave Width) displays the performance when adding the pulse width criterion to increase the specificity of P-wave detection. The performance of the morphology metric method is described previously in patent submissions, Far-field R-wave and P-wave discrimination, hereby referenced in their entirety. Detection of P-waves should be higher during closed loop operation than during open loop operation that is summarized in Table 1. Closed loop operation, as used herein, means that the algorithm uses AV synchrony to detect sensed P-waves followed by paced R-waves. In this type of operation, one can expect the algorithm to track P-waves for longer durations. The method used in the present invention for discriminating P-waves and R-waves has been described in U.S. Pat. No. 5,755,739, Adaptive and morphological system for discriminating P-waves and R-waves inside the human body, issued to Sun et al., and U.S. Pat. No. 5,778,881, Method and apparatus for discriminating P and R waves to Sun et al., both incorporated herein by reference in their totality.

It is to be understood that the above description is intended to be illustrative, and not restrictive. Many other embodiments will be apparent to those of skill in the art upon reading and understanding the above description. The scope of the invention should, therefore, be determined with reference to the appended claims, along with the full scope of equivalents to which such claims are entitled.

What is claimed is:

1. A software system implemented in a circuit for sensing P-waves in a pacemaker, the system in combination with the circuit comprising:

means for detecting a plurality of atrial depolarization P-wave signals wherein said means for detecting comprises at least two subcutaneous electrodes in data communication with means for pacing including a P-wave morphology detector; and means for pacing a ventricle synchronously with each one of said plurality of atrial depolarization P-wave signals detected by the at least two subcutaneous electrodes;

wherein said means for pacing further comprises at least one pacing lead and wherein a first of said at least one pacing lead is adapted to electrically couple to a ventricular chamber.

2. The system of claim 1 wherein said means for pacing is a single chamber ventricular-inhibited pacemaker.

3. The system of claim 2 wherein said pacemaker includes a hermetically sealed case including said at least two subcutaneous electrodes being peripherally distributed about the perimeter of the case.

4. The system of claim 2 wherein the at least one pacing lead comprises a ventricular pacing lead.

5. The system of claim 4 wherein said ventricular pacing lead is one of a unipolar pacing lead and a bipolar pacing lead.

6. A sensing circuit operating in co-operation with a pacemaker, a lead and at least one subcutaneous electrode array (SEA) implemented for pacing the ventricle synchronous with atrial depolarization signals, the circuitry comprising:

an analog to digital converter (ADC) for converting a plurality of cardiac depolarization signals;

a detector for detecting at least one of said plurality of cardiac depolarization signals coupled to said analog to digital converter (ADC);

a digital to analog converter (DAC) coupled to the detector to convert at least some of the signals passing through said detector;

a means for R-wave detection adapted to mechanically and electrically couple to a ventricular chamber; and a means for P-wave detection, wherein the means for P-wave detection is disposed on an external portion of an implantable medical device, and wherein signals from both the means for R-wave detection and signals from the means for P-wave detection are electrically coupled to a P-wave morphology detector having a single P-wave detection output signal and the P-wave detection signal in electrically coupled to said digital to analog converter (DAC).

7. The circuit of claim 6 wherein said circuit further comprises:

a plurality of signal inputs, wherein said plurality of signal inputs further comprise:

a signal input into said analog to digital converter (ADC) for a ventricular electrogram (VEGM) data signal from said lead;

a signal input into said analog to digital converter (ADC) for a electrocardiogram (EGG) data signal from said at least one subcutaneous electrode array (SEA); and a signal input into said analog to digital converter (ADC) for an electrocardiogram (EGG) data signal from an external lead.

8. The circuit of claim 7 wherein said ventricular electrogram (VEGM) data signal is transmitted via a ventricular lead.

9. The circuit of claim 7 wherein said electrocardiogram (EGG) data signal is transmitted from at least one external electrode such as from a programmer implemented to validate said electrocardiogram (EGG) data signal from said subcutaneous electrode array (SEA).

10. The circuit of claim 7 wherein said ventricular electrogram (VEGM) data signal include a plurality of intrinsic ventricular depolarization waveforms that inhibit at least one pre-scheduled ventricular output pulse.

11. The circuit of claim 7 wherein said electrocardiogram (ECG) data signal from the subcutaneous electrode array (SEA) is a primary input and provides the electrocardiogram (ECG) data signal to the analog to digital (ADC) on a substantially continuous basis.

* * * * *